United States Patent [19]

Callahan et al.

[11] 4,386,013
[45] May 31, 1983

[54] HYDROFORMYLATION PROCESS UTILIZING NOVEL CATALYST

[75] Inventors: Kenneth P. Callahan, Costa Mesa; Peter M. DiGiacomo, Mission Viejo; Martin B. Dines, Laguna Beach, all of Calif.

[73] Assignee: Occidental Research Corporation, Irvine, Calif.

[21] Appl. No.: 295,340

[22] Filed: Aug. 24, 1981

[51] Int. Cl.³ .............................................. B01J 31/24
[52] U.S. Cl. .............................. 252/431 P; 252/429 R; 252/431 C; 568/454; 260/429 R; 260/429.3
[58] Field of Search ............ 252/429 R, 431 P, 431 C

[56] References Cited

U.S. PATENT DOCUMENTS

| | | | |
|---|---|---|---|
| 3,637,627 | 1/1972 | Short et al. | 252/431 P X |
| 3,787,459 | 1/1974 | Frankel | 252/431 C X |
| 3,832,404 | 8/1974 | Allum et al. | 252/431 P X |
| 3,847,997 | 11/1974 | Allen | 252/431 P X |
| 3,900,557 | 8/1975 | Strathdee | 252/431 P X |
| 4,059,542 | 11/1977 | Jennings et al. | 252/431 P |
| 4,276,195 | 6/1981 | Verrade | 252/429 R X |
| 4,299,943 | 11/1981 | DiGiacomo et al. | 528/9 |

FOREIGN PATENT DOCUMENTS 10366 4/1980 European Pat. Off. .
10857 5/1980 European Pat. Off. .

*Primary Examiner*—Patrick Garvin
*Attorney, Agent, or Firm*—Robert J. Baran

[57] ABSTRACT

The instant invention relates to a novel hydroformylation catalyst comprising a composite of rhodium metal or a rhodium metal compound and a compound selected from the group consisting of compounds represented by the general formula $$M(O_3ZO_xR)_n$$

wherein M comprises a tetravalent metal, Z comprises a pentavalent atom, R is selected from the group consisting of organo radicals comprising a moiety selected from the group consisting of phosphine radicals; x is 0 or 1, and n is 2, provided that n is 1 when R is terminated with a tri- or tetra-oxy pentavalent atom. This catalyst is useful in hydroformylation processes which comprise contacting said catalyst with an olefin, at conditions sufficient to convert said olefin into an aldehyde or an alcohol. For example, 1-hexene may be hydroformylated to a mixture comprising heptylaldehyde isomers and propylene may be hydroformylated to n-butyraldehyde by means of a hydroformylation catalyst comprising a composite $RhCl(CO)(PC_6H_5)_2$ and $Zr(O_3PC_2H_5)_{4/3}[O_3P(CH_2)_3(PC_6H_5)_2]_{2/3}$.

13 Claims, No Drawings

HYDROFORMYLATION PROCESS UTILIZING NOVEL CATALYST

FIELD OF THE INVENTION

The instant invention relates to new catalysts which are useful in the hydroformylation of olefins such as alpha olefins. Both straight and branched olefins, especially $C_2$ to $C_{10}$ olefins may be converted into aldehydes and alcohols by the process and catalyst of the instant invention. For example, the conversion of propylene to n-butyraldehyde, a precursor for the preparation of di(2-ethylhexyl)phthalate (a polyvinyl chloride plasticizer) may be catalyzed by the novel catalyst.

BACKGROUND OF THE PRIOR ART

It is well known that various heterogeneous catalysts may be used to hydroformylate various olefins. Most commercial heterogeneous catalysts, however, are poorly characterized materials which have a distribution of active sites which exhibit variability in their nature, activity, and selectivity.

Despite these drawbacks, there are often significant process advantages accrued when a heterogeneous catalyst is employed. Homogeneous catalysts, which offer uniform composition and reactivity, and often fewer by-products, can present difficulties in separating product from the catalyst (an especially important point if the catalyst is based on a precious metal such as rhodium) and may have increased energy requirements. The advantages of both modes of reaction would be offered if one would attach a homogeneous catalyst to an insoluble backbone, a process termed heterogenization.

Heterogenization of a homogeneously active catalyst is not a new idea; quite a bit of work has already been carried out on this concept, but the previous supports have most often consisted of chemically-modified inorganic and organic polymers. These materials suffer from low chemical and thermal stability (due to the reactivity of the support), have a variety of active sites (like a conventional heterogeneous catalyst) due to the geometric irregularity of the polymer, and often exhibit leaching of the catalyst into the product stream, affording a separation problem similar to that of homogeneous catalysts. The layered zirconium phosphonates and analogous compounds (especially the layered species) have been found to be suitable support materials for compositing with active hydroformylation catalysts comprising rhodium metal and salts and other compounds thereof. The layered structure of such zirconium phosphonates and analogous compounds provide uniform catalytic sites and may be chemically modified to minimize leaching. Furthermore, more demanding processing conditions could be encountered without degradation of the support. Finally, the two-dimensional geometry of the interlayer space may result in an enhanced selectivity towards entering reactants or product formation.

BRIEF DESCRIPTION OF THE INVENTION

It has now been discovered that a novel hydroformylation catalyst comprising a composite of rhodium metal or a rhodium metal compound and a support selected from the group consisting of compounds represented by the general formula $$M(O_3ZO_xR)_n$$

wherein M comprises a tetravalent metal, Z comprises a pentavalent atom, R is selected from the group consisting of hydrogen and organo radicals provided at least a portion of such R groups comprise a moiety selected from the group consisting of phosphine radicals, X is 0 or 1, and n is 2, provided that n is 1 when R is terminated with a tri- or tetra-oxy pentavalent atom, may be used in a novel process to convert olefins into aldehydes and alcohols.

Z is preferably selected from the group consisting of members of Group V of the Periodic Table of the Elements having an atomic weight of at least 30; most preferably Z is P. That is, the compound that is composited with the rhodium metal or rhodium metal salt will comprise a compound selected from the group consisting of compounds represented by the general formulae $$M(O_3PO_xR)_n$$

M is preferably a tetravalent metal selected from the group consisting of metals with approximately the same ionic radius as $Zr^{+4}$ (0.8 Å), e.g.

| $Zr^{+4}$ | 0.80Å | $Te^{+4}$ | 0.81 | $Pr^{+4}$ | 0.94 | $Mn^{+4}$ | 0.5 |
|---|---|---|---|---|---|---|---|
| $W^{+4}$ | 0.66 | $Sn^{+4}$ | 0.71 | $Pb^{+4}$ | 0.92 | $Ir^{+4}$ | 0.66 |
| $U^{+4}$ | 0.89 | $Si^{+4}$ | 0.41 | $Os^{+4}$ | 0.67 | $Hf^{+4}$ | 0.81 |
| $Ti^{+4}$ | 0.68 | $Ru^{+4}$ | 0.65 | $Nb^{+4}$ | 0.67 | $Ge^{+4}$ | 0.53 |
| $Th^{+4}$ | 0.95 | $Pu^{+4}$ | 0.86 | $Mo^{+4}$ | 0.68 | $Ce^{+4}$ | 1.01 |

Most preferably, M is Zr.

Most preferably, the phosphine moiety will be capable of coordinating with the rhodium metal or the rhodium metal salt, to provide stability against loss of the hydroformylation activity of the above composite. For the purpose of this disclosure the term "capable of coordinating" shall mean the ability to form a covalent bond with the rhodium metal or rhodium metal compound.

Rhodium, as the metal or in a compound provides the hydroformylation activity in the above composite. Thus, active materials will be those that are known in the art as having suitable hydroformylation activity. For example, the following salts and other compounds comprising rhodium may be utilized to provide the hydroformylation activity $Rh_4(CO)_{12}$, $Rh_6(CO)_{16}$, $RhCl(CO) [P(C_6H_5)_3]_2$, $HRhCl_2[P(C_6H_5)_3]_3$, $HRh(CO) [P(C_6H_5)_3]_3$. As will be further discussed below, the support due to its unique structure provides an environment for obtaining certain advantages when used in combination with the rhodium metal or rhodium metal compound as a hydroformylation catalyst.

More specifically, the support is unique in providing a suitable environment for modification of the hydroformylation properties of rhodium metal compounds, i.e., the compounds which are useful as supports in the instant novel hydroformylation catalysts may exist in the form of layered structures, e.g., materials which exist in the form of sheets or slabs with a thickness of from 1 to more than 7 atomic diameters lined upon one another. In this structure relatively weak van der Waals or hydrogen bonding occurs between interlamellar basal surfaces in a direction perpendicular to the plane of the layers. In materials of this sort, guest molecules or ions such as the above rhodium metal and rhodium metal compounds can intercalate into the region between the layers. These materials may have properties which differ greatly from the starting layered compound. The compounds which are useful as a support in the instant hydroformylation catalysts can be further modified by the variation of the above-described R group. For example, R groups such as carboxylate, sulfonate, phosphonate, cyano, amino, alkenyl-containing groups, etc. can be utilized to further modify the hydroformylation properties of the instant catalysts.

The novel catalysts of the instant invention are especially useful in hydroformylation reactions wherein olefins, expecially alpha olefins, are converted into aldehydes and alcohols. For example, alpha olefins comprising up to 30 carbon atoms and which may be substituted with various heteroatom-containing groups may be converted into the corresponding aldehydes and alcohols. Substituents comprising the nitrogen and oxygen heteroatoms may be included in such substituents without interfering with the above hydroformylation reaction. The above-noted carbon atoms may reside in either aromatic, including condensed aromatic, alkyl, alkenyl, alkynyl, etc. groups. The reaction, however, will take place generally at the terminal olefin; that is, at the C-1 or C-2 carbon. The resulting product will comprise the corresponding aldehyde, but may also comprise some alcohol product as a result of hydrogenation of the aldehyde. Preferably, the alpha olefin will comprise from 2–10 carbon atoms and, other than the terminal olefin, is substantially saturated. For example, the relatively straight chain olefins, such as n-propylene, n-heptene, n-hexene, n-octene, etc. may be converted into the corresponding aldehydes and alcohols. In general, a mixture of the iso and the normal aldehydes will be obtained. In a preferred embodiment 1-heptene or propylene is converted into a mixture of the corresponding iso and normal aldehyde; that is, octylaldehyde and butyraldehyde, respectively. For example, propylene may be hydroformylated by the process of the instant invention to yield n-butyraldehyde which is a precursor for the preparation of di(2-ethylhexyl)phthalate; a well known polyvinyl chloride plasticizer.

The hydroformylation process utilizing the catalysts of the instant invention are conveniently carried out at temperatures of from 25° C. to 250° C., preferably from 75° C. to 175° C., and at pressures of from atmospheric to 800 atm, preferably from atmospheric to 100 atm. Feed rates of from 0.2 to 1000 volumes per hour per volume of catalyst and hydrogen and carbon monoxide addition of from about 200 to about 5000 standard cubic feet, respectively, per mole of olefin may be used.

DETAILED DESCRIPTION OF THE INVENTION

1. The Support

The compound or support useful in preparing the instant novel catalyst will be selected from the group consisting of compounds represented by the formula $M(O_3ZO_xR)_n$. In the above formula n may equal 1 or 2, except that n is 1 when R is terminated by a tri- or tetra-oxy pentavalent atom. M represents a tetravalent metal ion selected from the group consisting of

| | | | |
|---|---|---|---|
| Ar | Te | Pr | Mn |
| W | Sn | Pb | Ir |
| U | Si | Os | Hf |
| Ti | Ru | Nb | Ge |
| Th | Pu | Mo | Ce |

Z is an atom selected from the group consisting of the members of Group V of the Periodic Table of the Elements having an atomic weight of at least 30; R is selected from the group consisting of organic radicals comprising a moiety selected from the group consisting of phosphine and X varies from 0 to 1. Said phosphine radical-containing R groups should comprise at least about 1 mole % of said R groups, more preferably at least about 10 mole %. Because of the bulk of said R groups (as further described below) phosphino-containing R groups will generally not exceed about 50 mole %, if the desired layered structure for the support is to be obtained. More preferably, said compositing compound will be selected from the group consisting of the compounds represented by the general formula $M(O_3PR)_2$, or $M(O_3POR)_2$.

The above compounds may be prepared by a process which comprises reacting in a liquid medium, at least one acid compound having the formula

wherein k is 1 when n is 2 and k is 2 when n is 1, with at least one of the above tetravalent metal ions to precipitate a solid in which the molar ratio of pentavalent atom to tetravalent metal is about 2 to 1, the pentavalent atom is covalently bonded to R, (and when x equals 1, R is linked to the tetravalent metal through oxygen).

It should be noted that x will be 0 when the starting material for preparing the compound is represented by the general formula

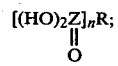

wherein n is 1 or 2, e.g.,

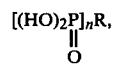

i.e., phosphorus acid or organophosphonic acids. When the starting material is represented by the general formula

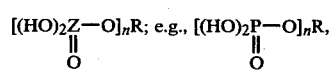

i.e., organophosphoric acids or phosphoric acid, x will be 1. If a mixture of such starting materials are used, x and n will vary from 0 to 1 and 1 to 2 respectively in accordance with the ratio of the starting materials.

The tetravalent metal M, and the pentavalent atom Z, may be selected in accordance with the desired support or compositing properties for the rhodium metal or rhodium metal compound by those skilled in the art. However, M is preferably Zr and Z is preferably P.

R is selected from the group consisting of organo acyclic, alicyclic, heteroacyclic, heterocyclic, aromatic groups, and mixtures thereof, provided the above noted phosphine moiety is present therein.

In general, R will be chosen to enable the composite compound to achieve a layered structure, whereby the rhodium metal or rhodium metal compound may be intercalated within such layers. Thus, the size of the R may be important, since very bulky R groups may disrupt such layering.

In general, with phosphorus as the pentavalent atom, the organo group should occupy no more than about 24 Å for proper spacing. This limitation is imposed by the basic crystal structure of zirconium phosphate. A spacing of 5.3 Å is known to exist between zirconium atoms in the zirconium plane of a crystal, a total area of about 24 Å$^2$ is known for the space bounded by zirconium atoms. It follows that any group anchored on each available site cannot have an area much larger than the site area and maintain the layered structure.

This limitation can be avoided through the use of a combination of larger and smaller groups, i.e., mixed components. If some of the sites are occupied by groups which have an area much less than about 24 Å$^2$, adjacent groups can be somewhat larger than 24 Å$^2$ and still maintain the layered structure of the compound.

The cross-sectional area which will be occupied by a given organo group can be estimated in advance of actual compound preparation by use of CPK space filling molecular models (Ealing Company) as follows: A model of the alkyl or aryl chain and terminal group is constructed, and it is situated on a scaled pattern of a hexagonal array with 5.3 Å site distances. Some areas which have determined by this procedure are listed in Table I.

TABLE I

| Moiety | Minimum Area (Å$^2$) | Moiety | Minimum Area (Å$^2$) |
|---|---|---|---|
| Alkyl chain | 15 | Isopropyl | 22.5 |
| Phenyl | 18 | t-butyl | 25 |
| Carboxyl | 15 | Chloromethyl | 14 |
| Sulfonate | 24 | Bromoethyl | 17 |
| Nitrile | 9 | Diphenylphosphino | 50 (approximately) |
| Morpholinomethyl | 21 | Mercaptoethyl | 13.5 |
| Trimethylamino | 25 | | |

Note that the bulk of the above-described phosphine moiety must also be included when calculating the correct R group size for attaining the preferred layered structure in the support.

One process for the formation of the support compound is a metathesis reaction conducted in the presence of a liquid medium receptive to the tetravalent metal ion at a temperature up to the boiling point of the liquid medium, preferably from ambient to about 150° C. and, more preferably, to about 100° C. at the pressure employed.

While water is the preferred liquid medium with phosphorus, as most of the organophosphorus acid compounds are hygroscopic, an organic solvent, such as ethanol can be employed, where water interferes with the reaction or where another pentavalent atom-containing acid is utilized in preparing the support. There need only be provided a solvent for the organo-substituted pentavalent atom-containing acid since the tetravalent ion can be dispersed as a solid in the solvent for slow release of the metal ion for reaction with the acid, e.g., the organophosphorus acid compound. If it has a sufficiently low melting point, the organo-substituted pentavalent atom-containing acid can serve as a solvent. Typically, the liquid medium is the liquid medium in which the organo-substituted pentavalent metal containing acid is formed.

To illustrate with acids, wherein phosphorus is the pentavalent atom, for complete consumption of the tetravalent compound, the amount of acid employed should be sufficient to provide two moles of phosphorus per mole of tetravalent metal. An excess is preferred. Phosphorus acid and/or phosphoric acid, if present, enters into the reaction and provides an inorganic polymer diluted in respect of the organo group in proportion to the amount of phosphorus or phosphoric acid employed.

Reaction is virtually instantaneous at all temperatures leading to precipitation of layered crystalline, semi-crystalline or amorphous solid compounds.

R will also be selected in accordance with the properties of the hydroformylation catalyst which is desired. For example, the R group may be selected for its ability to coordinate with the rhodium metal or rhodium metal compound through the phosphine radicals. The R groups may include heteroatoms suitable for assisting in or providing for additional coordination. For example, R groups containing amino, cyano, sulfono, mercapto, halide, carboxy, ether, etc. groups may be utilized.

Since it is well known that rhodium is a very valuable metal, the above R group will be tailored to provide an environment from which the rhodium, either as the metal or the compound, will not be substantially leached during the hydroformylation process being carried out. While the phosphine moiety, to a certain extent, prevents rhodium leaching (by means of a coordination bond formed with either the metal or the salt) further protection from leaching is desirable. Thus, at least some R groups may be chosen so that they form "pillars" between various layers. As further described below, the pillars may include Rh as a covalently or ionically bound moiety. These pillars which are formed by utilizing difunctional or bis acids as the pentavalent element containing acid compound. For example, in the case of Z being P, bis-organophosphonic acids or bis-organophosphorus acids will be utilized to provide at least some of the R groups. Examples of suitable bis-organophosphonic acids for use in preparing layered compounds comprising pillars, include

wherein a and b are ingers of from about 1 to about 20.

In addition, or in place of, the above pillars, one can exchange various bis-phosphonic acids with layered zirconium phosphonates after formation to provide a pillar at the edges of the various layers. This structure has been terminated a "bird cage" or "jail cell". In particular, after the intercalation of the rhodium into the layered zirconium phosphonate the intercalated solids may be contacted with a solution comprising a bis-phosphonic acid. The bis-phosphonic acid will exchange with various pendant R groups to form pillars at the edge of such layers thereby trapping the rhodium in between the layers.

2. The Group VIII Metal or Group VIII Metal Compound

Rhodium metal or a rhodium metal compound is the active moiety in the instant novel catalyst. Rhodium is active either as a compound, e.g., a salt or the metal form. For example, various complex salts including halogen salts of rhodium metals are useful hydroformylation moieties. Other examples of useful rhodium metal salts include acetates, acetylacetonates, nitrates, etc.

The rhodium may also be provided as a complex wherein the rhodium exists in the zero valence state and, thus, is not correctly labeled as a salt. For example, carbonyl complexes, and various other complexes such as phosphines or mixed-ligand species of rhodium are known active hydroformylation moieties.

In general, any known catalyst, either heterogeneous or homogeneous may be composited with the above support compounds to provide novel catalysts.

3. The Hydroformylation Catalyst

The above support compound may exist as a layered structure. It is possible to intercalate guest species in between such layers. As is noted herein, intercalation is affected by the nature of the region between the various layers. Rhodium metal and various rhodium metal compounds, which are active hydroformylation moieties, are suitable for intercalation between the layers of the above described support compounds. Such rhodium metal and rhodium metal compounds may form bonds with the appended phosphine group containing R. The instant novel hydroformylation catalyst may comprise from about 0.5 to about 20, weight %, Rh in combination with from about 0.1 to about 10 moles phosphine per gm-atom of Rh.

4. Preparation of the Hydroformylation Catalyst

The above support compounds may be contacted with a solution comprising the active moiety, i.e., the rhodium metal or rhodium metal compound or a precursor thereof, for a time sufficient to enable such moiety to intercalate into the layers of such support compound. The solvent for dissolving said moiety or precursor (if a solvent is necessary) may be aqueous or non-aqueous, since in general the composite is stable to both types of solvents. The composites are unstable in the presence of aqueous alkali; therefore, solutions having a pH of at most 8 should be utilized for preparing the instant novel hydroformylation catalyst. Liquid or gaseous rhodium compounds may be intercalated directly into the above-described layered compounds without the benefit of a solvent. The hydroformylation catalyst prepared by intercalation alone are not preferred since as demonstrated below, these catalysts tend to lose rhodium by leaching into the olefin-containing reactant stream.

Alternatively, the rhodium may be incorporated into the composite during the formation of the composite itself. For example, the R group may contain rhodium covalently or ionically bonded thereto. For example, as shown below, a complex of rhodium and one or more phosphine containing radicals having a reactive trimethylsilyl radical may be reacted with a tetravalent ion such as zirconium ion under conditions wherein a layered compound comprising rhodium in the R-group is formed in-situ. This process for preparing the layered compounds of instant invention is analogous to the process described in U.S. patent application Ser. No. 133,859, now U.S. Pat. No. 4,299,943, entitled "Nonaqueous Preparation of Layered or Amorphous Organometallic Inorganic Polymers", which was filed on Mar. 25, 1980, in the names of DiGiacomo et al., which is herein incorporated by reference for teaching methods for incorporating the rhodium in the above-described in-situ process. Note as demonstrated in Example 5 below, other trimethylsilyl containing materials may be reacted along with the aforementioned phosphine-containing materials to form a layered compound wherein some of the R groups will contain rhodium while the remainder will not.

In general, the "in-situ" process for preparing the instant novel hydroformylation catalyst comprises reacting a diester of an organo-substituted pentavalent atom-containing acid of the formula $$[(R'O)_2OZ]_kR''$$

wherein

R' is a silyl group, e.g. a trimethylsilyl group; Z and k are as defined above and R'' comprises Rh coordinated to one or more, e.g. two phosphino radicals; with a compound comprising the above tetravalent metal M to precipitate a solid compound of the formula $M(O_3ZO_x)_2R''$. Preferably, k is 2 and R'' comprises a radical selected from the group consisting of radicals represented by the general formula

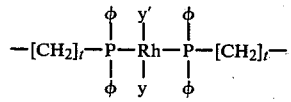

wherein t is an integer of from 1 to about 10, e.g. from about 2 to about 3; and y and y' are ligands capable of coordinating with Rh, e.g., CO, Cl, $\phi_3 P$, etc; y and y' can be the same ligand. When R'' is one of the above preferred compounds, hydroformylation catalysts which are resistant to leaching of rhodium are obtained. These catalysts have been described below as "pillared" rhodium catalysts.

The resistance to leaching of the rhodium can also be increased by the use of the "jail-celling" technique described below.

The preferred hydroformylation catalyst, which comprises a rhodium moiety having catalytic activity intercalated between the layers of a layered crystalline material selected from the support compounds described above, said catalyst being characterized as resistant to egress of said rhodium moiety from between said layers, may be prepared by a process which comprises the steps of (a) intercalating a rhodium moiety having catalytic activity, or a precursor thereof, into the layers of the above described support compound, wherein said compound is characterized as a layered crystalline material comprising contiguous layers, each of said layers being spaced from and substantially unconnected to its neighboring layer to thereby allow access of said rhodium moiety or precursor thereof into the interior of said crystalline material, and (b) crosslinking said layers to thereby connect said contiguous layers to neighboring layers and hinder egress of said rhodium moiety or precursor thereof from the interior of said crystalline material.

Preferably the crosslinking is effected by means of a bis acid compound such as a bis acid having the general formula

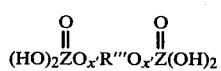

wherein Z is as described above, x' is 0 or 1, and R''' is an organoradical such as the organo radicals described above. More preferably, Z is P and x' is 0.

The crosslinking may be carried out by contacting the solid intercalated compound with the bis acid in solution, e.g., an aqueous solution, for a time and at conditions sufficient to effect exchange of some of the interlayer R or O—R groups of the intercalated compound for the bis acid. Conveniently the contacting may be effected at ambient temperature and pressure.

Finally, the hydroformylation catalysts prepared by any of the aforesaid methods may be activated by separating the intercalated support from the rhodium metal or rhodium metal compound or precursor containing solution and removing said excess solvent by drying at a temperature of from about 25° to about 200° C. for a time sufficient to remove substantially all of said excess solvent. Said drying may take place in air or an inert atmosphere or under vacuum. The composite of the support and the rhodium metal containing compound, etc., may be activated for hydroformylation by contacting said dried catalyst with a reducing atmosphere, e.g., hydrogen gas, at room temperature or an elevated temperature of from about 25° C. to about 200° C., preferably from about 50° C. to about 150° C., for a time sufficient to convert said rhodium metal compound or precursor into an active hydroformylation moiety.

The following are specific examples of the instant invention. There is no intention that the scope of the instant invention may be limited to the examples, since there are many variations thereon which are within the ordinary skill of the art.

EXAMPLE 1

Preparation of diethyl (3-diphenylphosphinopropyl) phosphonate

In the dry box a quartz tube 10 mm O.D.×275 mm long was charged with 9.782 g (54.9 mmol) diethylallylphosphonate and 10.222 g (54.9 mmol) diphenylphosphine. After thoroughly mixing there two components the tube was capped with a ground glass joint equipped with a stopcock, removed from the dry box and evacuated with an oil pump. The reaction mixture was then photolyzed for 24 hrs. using a 288 watt long wavelength ultraviolet lamp and external water cooling. Proton nmr analysis of the resulting product indicated that the desired product had been formed in >90% yield, the major contaminant being unreacted diphenylphosphine (no unreacted allyl phosphonate was observed).

Diethyl(2-diphenylphosphinoethyl)phosphonate was prepared from diethylvinylphosphonate in similar yield using this method.

EXAMPLE 2

Preparation of ethyl-diluted zirconium bis(3-diphenylphosphinopropyl)phosphonate A nitrogen-filled 250 ml three-necked round-bottom flask was charged with 18.244 g (109.8 mmol) of diethyl ethylphosphonate fitted with an L-shaped addition tube having a stopcock and a 125 ml pressure-equalizing addition funnel, and placed in the dry box. In the box the flask was charged with 20.0 g (54.9 mmol) of diethyl(3-diphenylphosphinopropyl)phosphonate prepared as above, and 65.921 g (330 mmol) trimethylsilyl iodide was put in the addition funnel. Out of the dry box the Me$_3$SiI was added dropwise to the stirring phosphonate mixture over a 30 min. period; the reaction flask was cooled by immersion in an ice water bath. The resulting mixture (which comprised

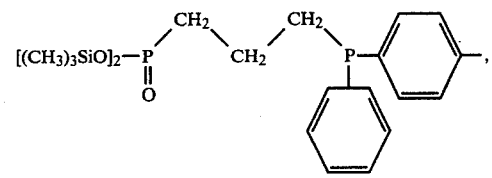

in admixture with the trimethylsilyl iodide derivative of diethylethylphosphonate) was allowed to warm to room temperature and stirred at a temperature for 30 min. before 50 ml H$_2$O was added. After a further 30 min. stirring the aqueous phase was extracted into a solution of 20.615 g (82.4 mmol) ZrOCl$_2$.4H$_2$O in 200 ml H$_2$O. A white precipitate formed immediately. The reaction mixture was heated to reflux for 18 hr., cooled, and the solid was filtered through a medium porosity frit, washed with water and acetone, and dried to constant weight using an oil pump vacuum. Yield: 31.03 g, 86%, ethyl-diluted zirconium bis(3-diphenylphsophinopropyl)phosphonate.

EXAMPLE 3

Loading of Rhodium Into Layered Zirconium Phosphine Phosphonates

In the dry box a 100 ml Schlenk flask was charged with 1.818 g (4.14 mmol) of the Zr(O$_3$PC$_2$H$_5$)$_{4/}$-$_3$[O$_3$P(CH$_2$)$_3$P$\phi_2$]$_\frac{3}{8}$ of Example 2. Out of the dry box 75 ml of benzene and 1.907 g (2.76 mmol) of RhCl(CO)(P$\phi_3$)$_2$ were added to the flask under a stream of nitrogen. The originally yellow solution began to turn orange after 5 min. and slowly deepened in color. The reaction mixture was allowed to stir at room temperature for 6 days, and the brown solid was separated by filtration through a fine porosity frit, washed with 50 ml benzene and dried in vacuo. The resulting solid weighed 1.844 g and exhibited a band in its infrared spectrum at 1945 cm$^{-1}$ assigned to Rh—CO. Anal. Calcd (on the basis of weight gain): Rh, 0.34%; found: Rh, 0.71%.

EXAMPLE 4

Preparation of

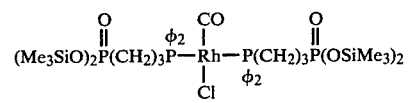

A 50 ml 3-necked round-bottom flask was charged with 4.61 g (12.65 mmol) of diethyl(3-diphenylphosphinopropyl)phosphonate in the dry box, and 5.063 g (25.30 mmol) trimethylsilyl iodide was added to it over a 15 min. period. The capped flask was then removed from the dry box and the solution was allowed to stir for another 30 min. The flask was then attached to a vacuum pump through a trap and ethyl iodide was removed by pumping for 2.5 hr. at 0.25 mm Hg pressure (heating with a warm water bath for the last 15–30 min. was useful in removing the last traces of ethyl iodide). A proton nmr spectrum of a portion of the gummy product dissolved in CD$_3$CN was in very good agreement with that expected.

The product was dissolved in 100 ml methylene chloride, and to this solution 0.780 g (2.01 mmol) [Rh(CO)$_2$Cl]$_2$ was added under nitrogen. A vigorous reaction ensued: gas was evolved and the solution turned deep red. The reaction mixture was allowed to stir at room temperature for 30 min., after which the solvent was removed by rotary evaporation. An infrared spectrum of the resulting solid showed bands at 1970 cm$^{-1}$ ($\nu$Rh—CO) and 1250 cm$^{-1}$ ($\nu$Si—O).

EXAMPLE 5

Preparation of
Zr(O$_3$PC$_2$H$_5$)$_{18/11}$[O$_3$P(CH$_2$)$_3$P$\phi_2$RhCl(CO)P$\phi_2$(CH$_2$)$_3$PO$_3$]$_{2/11}$ The rhodium complex prepared in Example 4 above was dissolved in 100 ml methylene chloride, and bis(trimethylsilyl) ethyl phosphonate prepared from 6.004 g (36.13 mmol) diethyl ethyl phosphonate and trimethylsilyl iodide was added to it. This mixture was stirred for a few minutes before 8.126 g (22.08 mmol) zirconium propoxide was added dropwise under N$_2$. A deep brown gel formed about 5 min. after the addition was complete. An additional 100 ml methylene chloride was added to fluidize this gel, and the reaction mixture was allowed to stir at room temperature for 87 hrs. It was then filtered through a medium porosity frit, and washed with 12 25-ml portions of CH$_2$Cl$_2$. As the final wash was still not colorless the solid was transferred to a Soxhlet extraction thimble and was continuously extracted with methylene chloride for 16 hrs. At this point fresh solvent was added to the extractor, and no further loss of color to the solvent was seen after three more extractions. The orange-brown product was dried in air. Its infrared spectrum was poorly resolved, but a band at 1960 cm$^{-1}$ assigned as Rh—CO was present. Anal. Found: Rh, 2.69%.

EXAMPLE 6

Preparation of

(EtO)$_2$PCH(P$\phi_2$)CH$_2$P$\phi_2$

To a 250 ml reaction flask was added 7.71 g diethyl vinyl phosphonate and 30 ml carbon tetrachloride. A slight excess (2.4 ml) of bromine was added, and the resulting solution was allowed to stir for 30 min. before excess Br$_2$ and solvent were removed by rotary evaporation. An infrared spectrum of the residue showed no C═C absorption, indicating that all the vinyl groups had been brominated. The product was dissolved in THF and cooled with ice water.

In a separate reaction vessel 17.50 g HP$\phi_2$ in 50 ml tetrahydrofuran (THF) was reacted with hexane-washed NaH. A considerable amount of gas was evolved. The reaction mixture was heated to a mild reflux for about 1 hr., then the red solution was cooled to room temperature and transferred to an addition funnel under nitrogen, which was then attached to the flask containing the bromination product.

Slow addition of the NaP$\phi_2$ solution to the

(EtO)$_2$PCHBrCH$_2$Br solution gave an exothermic reaction, the solution was decolorized, and solids were observed to form. After stirring 1 hr. the mixture was brought to room temperature and the solid was filtered and washed with THF. The crude product was obtained by rotary evaporation of the filtrate as a heavy oil. Despite several attempts we were not able to crystallize this product. The yield, based on the NaBr collected, was 82.5%.

EXAMPLE 7(a)

Preparation of Chelated Rhodium Catalyst

In a mixture of 75 ml carbon tetrachloride and 20 ml chloroform were combined 3.59 g of

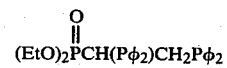
(EtO)$_2$PCH(P$\phi_2$)CH$_2$P$\phi_2$ made as in Example 6 and 4.46 g diethylethylphosphonate. This mixture was cooled in an ice bath at 10 ml (CH$_3$)$_3$SiI was added dropwise. It was stirred for 30 min., then by-product ethyl iodide was distilled off using an oil pump. The resulting product was separated into two equal fractions, and to one of them was added 100 ml THF. An addition funnel containing 0.66 g [Rh(CO)$_2$Cl]$_2$ dissolved in 25 ml THF was attached to this flask, and the rhodium solution was added dropwise. The color of the reaction mixture changed to yellow, then deep red over a 10 min. period, and after 20 min. more the color was coffee brown. After 1 hr. reaction the THF was distilled off at 0.3 mm, and 100 ml distilled water was added to the residue. Not all dissolved, even on heating to 55°, so 125 ml THF was added until everything was in solution. Next a solution of 2.02 g ZrOCl$_2$.4H$_2$O in 25 ml H$_2$O was added, and a dark solid precipitated. The solid was filtered and washed with H$_2$O and THF; the latter washings were highly colored. After drying in a vacuum desiccator the solid was placed in a Soxhlet extraction thimble and continuously extracted with methylene chloride overnight, then dried in a desiccator. Anal. Calcd. Zr. 17.50; P, 16.65; C, 32.27; H, 3.33; Rh, 7.90. Found: Zr, 16.38; P, 15.67; C, 27.95; H 3.63; Rh, 2.82.

EXAMPLE 7(b)

Preparation of Bis-Chelated Rhodium Catalyst

The same general procedure as described in Example 7(a) was used, but the phosphine, rhodium ratio of the starting materials was increased to 4:1. The resulting product exhibited no band in its infrared spectrum for a rhodium carbonyl group, which indicated the probability that the metal was bound to all four phosphine groups.

EXAMPLE 8

Preparation of 1,6-hexanediolbis(6-bromohexanoate)

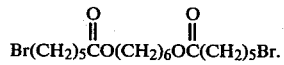
Br(CH$_2$)$_5$CO(CH$_2$)$_6$OC(CH$_2$)$_5$Br.

A 100-ml round-bottom flask was charged with 30 ml toluene, 12.48 g (64 mmol) 6-bromohexanoic acid, 3.78 g (32 mmol) 1,6-hexanediol, and 5 drops conc. sulfuric acid. The flask was connected to a Dean-Stark trap and heated to reflux temperature for 3.5 hrs., at which time an additional 10 drops of conc. sulfuric acid was added.

The reaction mixture was taken back to reflux for an additional 2.5 hrs., when no further evolution of water was observed. The reaction mixture was cooled to room temperature and used directly for the next reaction step.

EXAMPLE 9

Preparation of 1,6-hexanediolbis(6-diethylphosphonatohexanoate)

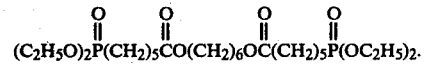

To the reaction mixture described above was added 11.6 ml (68 mmol) of triethyl phosphite, and the resulting solution was heated to reflux overnight. The next morning the mixture was vacuum distilled to remove all volatile materials. The remaining oily product (14.6 g, 78% yield for the two steps) was shown to be the desired product by infrared and proton nmr spectra.

EXAMPLE 10

Preparation of 1,6-hexanediolbis[6-bis(trimethylsiloxy)phosphonatohexanoate]

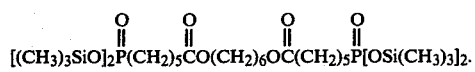

The material prepared as described above was placed in a 100 ml Schlenk flask to which was attached a dropping funnel containing 19.5 g (97.5 mmol) of trimethylsilyl iodide. The flask was cooled to 0° C. using an ice water bath and the trimethylsilyl iodide was added dropwise with stirring over a 30 min period. The cooling bath was then removed and the reaction mixture was warmed to room temperature and let stir for an additional 90 min. An oil pump was connected to the reaction vessel through a cold trap and the volatile side products were removed from the main product in this manner. The resulting yellowish oil weighed 19.0 g (100% yield.).

EXAMPLE 11

Preparation of

A 100 ml round-bottom flask equipped with a Friedrichs condenser and a stirring bar was loaded with 1.47 g (2.11 mmol) of the trimethylsiloxy ester described above, 20 ml of acetonitrile and 20 ml of water. The resulting slightly cloudy white solution was stirred for 10 min., whereupon a solution of 1.05 g (4.21 mmol, 100% excess) of $ZrOCl_2 \cdot 4H_2O$ in 20 ml of water was added. A white precipitate formed immediately. The suspension was taken to reflux for 2 hrs., cooled, and the solid was filtered and washed successively with 10 ml of water, 2×20 ml of acetone, and 20 ml of diethyl ether. The resulting solid weighed 0.47 g, corresponding to a yield of 40% based on the ester charged.

EXAMPLE 12

Preparation of 1,6-hexanediolbis(6-phosphonohexanoate)

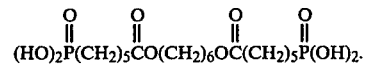

To a 100 ml round-bottom flask was charged ca. 7 g of the trimethylsiloxy ester described in Example 10 above, and 10 ml of acetonitrile and 35 ml water were added to it. The reaction mixture was taken to reflux for 1.5 hrs., at which time two layers were apparent. Addition of 20 ml acetonitrile made the layers miscible again. The mixture was taken to reflux for an additional 30 min., 25 ml more water was added, and the solution was boiled a further 10 min. The solvent mixture was removed by rotary evaporation. Two layers appeared again. The top layer was shown to be hexamethyldisiloxane, and it was separated from the bottom layer. Further evaporation again led to the formation of two layers; this time the top layer was shown to be water. It was separated, and on cooling, the bottom layer crystallized. The resulting solid was filtered, washed with water, air dried, and then recrystallized from water. Infrared and proton nmr spectra confirmed the formulation.

EXAMPLE 13

Preparation of "Jail-celled", Intercalated Rhodium Catalyst

A suspension of 0.353 g of the intercalation product of $Zr(O_3PC_2H_5)_{4/3}[O_3P(CH_2)_3P(C_6H_5)_2]_{2/3}$ and $RhCl(CO)[P(C_6H_5)_3]_2$ prepared as described in Example 3, 2.360 g of 1,6-hexanediolbis-(6-phosphonohexanoate), prepared as described in Example 12 above, 50 ml water and 10 ml acetonitrile was prepared and heated to reflux for 110 minutes, then cooled, filtered, and washed with 3×20 ml acetone, followed by 2×20 ml diethyl ether. Infrared analysis of the solid showed a strong absorption at 1750 cm$^{-1}$ assigned to the ester carbonyl group. It is believed that a cross-linking reaction occurred at the edges of the layered solid support, which reaction served to decrease the leaching of rhodium from the catalyst support. A similar reaction is believed to have occurred in Example 14 below.

EXAMPLE 14

General Procedure for Hydroformylation

Catalyst (Ca. 0.2 g) was suspended in 20 ml hexane in the glass liner of a Parr stainless steel bomb, then the reactor was assembled and sealed. The bomb was pressurized to 200 psi with CO and vented three times to remove ambient air. Propylene was then charged to its tank pressure (80 psig), followed by CO and $H_2$ in the desired ratios and pressures. The bomb was heated to working temperature using the Parr heating mantle, and the bomb internal pressure was monitored as a function of time with the attached gauge. After a suitable time the reactor was cooled to room temperature, a gas sample (if desired) was collected, the gas pressure was vented and the product mixture was separated from catalyst by filtration. The liquid filtrate was analyzed by gas chromatography.

The following hydroformylation reactions were carried out using the catalyst of Example 3.

TABLE 1

Rhodium Anchored on Zirconium Phosphonate as a Hydroformylation Catalyst

| SUBSTRATE | PRESS., TEMP, TIME | CONVERSION | TURNOVER NO.[a] |
|---|---|---|---|
| 1-HEXENE | 1200 PSI, 100°, 5 Hr | 60% | 250 Hr[−1] |
| PROPYLENE | 1245 PSI, 130°, 5¼ Hr | 69% | 322 Hr[−1] |
| COMPARATIVE DATA | | | |
| A. POLYMER-ANCHORED RHODIUM[b] | | | |
| 1-PENTENE | 800 PSI, 60°, 18 Hr | 100% | 5.4 Hr[−1] |
| B. HOMOGENEOUS RHODIUM[c] | | | |
| 1-PENTENE | 250 PSI, 40°, 3 Hr | 74% | 21 Hr[−1] |

Results of product analysis are shown in Table 2. It can be seen that the instant catalyst has less n:iso specificity than the homogeneous system under the conditions studied.
Note that the ratio of linear to branched isomers may be improved by the addition of additional phosphine.
[a] No. of moles of reactant converted into product per atom of rhodium.
[b] See Catalyst 3A, a diphenylphosphinopolystyrene-divinyl-benzene resin exchanged with RhH(CO) (Pϕ₃)₃, "Aldehyde and Ketone Synthesis Using Polymer-Bound Rhodium Catalyst III"; Pittman, et al, Ann. N.Y. Acad. Sci., 239, 76 (1974)
[c] RhH(CO) (Pϕ₃)₃, as reported in the reference cited in [b] above.

TABLE 2

Products Obtained From Anchored Rhodium Catalysts Substrate

| SUBSTRATE | PRODUCTS | |
|---|---|---|
| 1-HEXENE | 95% | HEPTALDEHYDES (EQUIMOLAR MIX OF n-HEPTANAL; 2-METHYLHEXANAL; AND 2-ETHYL PENTANAL) |
| | 5% | ALDOL CONDENSATION PRODUCTS, e.g. 12 CARBON HYDROXY ALDEHYDES |
| PROPYLENE | 91% | BUTYRALDEHYDES LINEAR:BRANCHED = 6:5 |
| | 9% | ALDOL PRODUCTS, e.g. 8 CARBON HYDROXYALDEHYDES LINEAR: BRANCHED RATIO INCREASED TO 8:5 IN THE PRESENCE OF EXCESS Ph₃P |

The resulting product stream from the above reactions had high rhodium content due to leaching of the precious metal by solvent, reactants and/or products.

This problem was somewhat alleviated by anchoring the rhodium catalyst more tightly to the layered compound in a double-bound arrangement. This route entailed preparation of rhodium complexes of phosphine-substituted phosphonic esters which were subsequently reacted with Zr(IV) to form the layered catalysts (See Example 5(a) above). This species is termed a "pillared rhodium" hydroformylation catalyst. Also, the leaching of rhodium can be decreased by "jail-celling" in accordance with Example 13.

Catalytic runs were carried out using both exchanged (intercalated) pillared, and "jail-celled" catalysts. The resulting product liquids were filtered through 0.2µ pore size paper to remove catalyst fines, and then analyzed for rhodium content. The results, presented in Table 3, indicate a substantial decrease in rhodium leaching when the pillared catalyst is used, and a further decrease when the "jail-celled" catalyst is used.

TABLE 3

RHODIUM CONTENT OF PRODUCT LIQUIDS[a]

| Catalyst | Rhodium content, mg/L |
|---|---|
| Exchanged rhodium | 35.7 |
| Pillared rhodium | 0.12 |
| Jail-celled exchanged rhodium | 0.07 |

[a] Reaction conditions: 20 ml hexane solvent. 0.2g catalyst, 80 psig propylene. 340 psig H₂, 340 psig CO, 135° C., 5–6 hr.

The prior art rhodium catalyst gives optimum production of linear aldehyde when the temperature is low (100° C.), the total pressure is low (20 atm), the H₂:CO feed ratio is greater than stoichiometric (3:1), a large excess of phosphine is present (200 mol/mol rhodium), and in a polar solvent. All of these parameters were varied using the instant catalysts and it was found that the instant catalyst is less sensitive to operating conditions than is the homogeneous catalyst. Details are presented in Table 4. Conversion of propylene was in the 80% range in most cases.

The catalyst used in Examples a–f was prepared by the method described in Examples 1–3 above with the proviso that hexyl is substituted for up to 80 mole % of the corresponding ethyl reactant in Examples b, e and f. Of course, in Example c, hexyl is substituted in total for the corresponding ethyl reactant. Example d is an example of the jail-cell catalyst which was prepared in Example 13.

See Example 5 for the preparation of the "pillared" catalyst utilized in Examples g, h and i.

The catalyst used in experiments j through n is described in Example 7(a) with the analogous carboxyethyl reactant being substituted for 100 mole % of the ethyl reactant to provide the carboxyethyl functionality. See U.S. Pat. No. 4,235,990 herein incorporated by reference, to show the preparation of a carboxy ethyl functional inorganic polymer useful as a support in the process of the instant invention.

The catalyst used in experiments o, p and q was the catalyst prepared in Example 7(b) with 100 mole % of the carboxyethyl reactant being substituted for the ethyl reactant to provide carboxy ethyl functionality.

TABLE 4

HYDROFORMYLATION OF PROPYLENE BY THE INSTANT RHODIUM CATALYSTS

| Example | T, °C. | P, psig | CO:H₂ | Solvent | Diluent R Group[a] | linear: branched |
|---|---|---|---|---|---|---|
| Rhodium Exchanged Catalyst | | | | | | |
| a | 130 | 880 | 1:1 | toluene | ethyl | 1.11 |
| b | 130 | 760 | 1:1 | toluene | ethyl + hexyl | 0.86 |
| c | 130 | 880 | 1:1 | toluene | hexyl | 1.29 |
| d | 130 | 880 | 1:1 | toluene | ethyl | 1.34[b] |
| e | 80 | 320 | 1:2 | toluene | ethyl + hexyl | 0.73 |
| f | 150 | 320 | 1:2 | toluene | ethyl + hexyl | 0.86 |
| Pillared Rhodium Catalyst | | | | | | |
| g | 130 | 880 | 1:4 | hexane | ethyl | 0.91 |
| h | 130 | 880 | 1:1 | hexane | ethyl | 0.82 |
| i | 60 | 480 | 1:1 | hexane | ethyl | 1.04 |
| Chelated Rhodium Catalyst | | | | | | |
| j | 130 | 880 | 1:1 | hexane | carboxyethyl | 0.85 |
| k | 130 | 880 | 1:1 | hexane | ethyl | 0.85 |
| l | 80 | 280 | 1:1 | dimethyl formamide | ethyl | 2.56[c] |
| m | 80 | 200 | 1:2 | dimethyl formamide | ethyl | 5.56[c] |
| n | 130 | 880 | 1:1 | hexane | carboxyethyl | 0.92[b] |
| Bis-Chelated Rhodium Catalyst | | | | | | |
| o | 130 | 880 | 1:1 | hexane | carboxyethyl | 1.25 |
| p | 80 | 200 | 1:2 | hexane | carboxyethyl | (very slow reaction) |
| q | 130 | 760 | 1:0.9 | hexane | carboxyethyl | 1.25 |

[a] The phosphine radical containing R group was 3-diphenylphosphino propyl.
[b] jail-celled
[c] Excess of 20 moles triphenylphosphine per gm-atom of Rh added to reactant stream.

It can also be seen that the linear:branched product ratio is not greatly affected when other variables, such as CO:H₂ ratio, total pressure or temperature are altered. These results indicate that the catalysis observed is not due to homogeneous rhodium species, for they are strongly affected by such changes. They also indicate that when rhodium is anchored to zirconium phosphonate its catalytic behavior is substantially altered from that in solution.

A more sterically confining atmosphere around the rhodium without adding external phosphine, results from replacing the ethyl diluent with a larger group, hexyl. A small increase in selectivity to the linear isomer was observed, by such replacement although activity was decreased. It was believed that the hexyl groups might be too large, and impair accessibility to the catalytic sites, and, therefore, a ternary compound was prepared which had both ethyl and hexyl diluents. The activity of the catalyst was substantially improved, but the selectivity was inverted and the branched product was formed in greater amounts than the desired linear isomer.

It was also sought to increase the polarity of the medium surrounding the catalyst without using a polar solvent (which could increase the leaching of rhodium from the solid). The approach chosen was to use polar groups, i.e. carboxyethyl groups on the diluents. No significant change in specificity was observed when this modification was introduced.

Increased specificity was observed in catalytic reactions employing the bis-chelated catalysts and the product liquids exhibited no catalytic activity, signifying no leaching of rhodium into the product stream. These solids had lower activity, however, which may reflect impaired accessibility of the catalytic sites or decreased catalytic activity of the rhodium due to its altered structure.

What is claimed is:

1. A hydroformylation catalyst comprising a composite of rhodium and a support selected from the group consisting of compounds represented by the general formula $$M(O_3ZO_xR)_n$$

wherein M comprises a tetravalent metal, Z comprises an atom selected from the group consisting of members of Group V of the Periodic Table of the Elements having an atomic weight of at least 30, R is selected from the group consisting of organo acyclic, alicyclic, heteroacyclic, heterocyclic, aromatic groups and mixtures thereof, provided that at least some of such organo radicals comprise a moiety selected from the group consisting of phosphine radicals, x is 0 or 1, and n is 2, provided that n is 1 when R is terminated with a tri- or tetra-oxy pentavalent atom.

2. The catalyst of claim 1 wherein M is selected from the group consisting of Zr, W, U, Ti, Th, Te, Sn, Si, Ru, Pu, Pr, Pb, Os, Nb, Mo, Mn, Ir, Hf, Ge, Ce and mixtures thereof.

3. The catalyst of claim 2 wherein said moiety is coordinated with said rhodium.

4. The catalyst of claim 3 wherein M comprises Zr and Z comprises P.

5. The catalyst of claim 1 wherein said compound is characterized as having a layered structure comprising two or more layers, each layer being separated from the adjacent layer by from about 6 Å to about 50 Å.

6. The catalyst of claim 5 wherein said rhodium is intercalated between said layers.

7. The catalyst of claim 6 wherein said rhodium is coordinated with said phosphine moiety.

8. The catalyst of claim 7 wherein said phosphine moiety comprises a diphenyl phosphine radical.

9. A process for preparing a hydroformylation catalyst which process comprises the step of reacting at least one compound of the formula $$((R'O)_2OZO_x)_kR''$$

wherein R' comprises a silyl radical, Z comprises an atom selected from the group consisting of members of Group V of the Periodic Table of the Elements having an atomic weight of at least 30, x and k are 0 or 1, and R'' comprises rhodium coordinated to one or more phosphino radicals with a compound comprising a tetravalent metal M, wherein M is selected from the group consisting of Zr, W, U, Ti, Th, Te, Sn, Si, Ru, Pu, Pr, Pb, Os, Nb, Mo, Mn, Ir, Hf, Ge, Ce and mixtures thereof to precipitate a solid hydroformylation catalyst represented by the general formula $$M(O_3ZR'')_n$$

wherein n is 1 when k is 2 and n is 2 when k is 1.

10. The process of claim 9 wherein R' is trimethylsilyl, Z is P and M is Zr.

11. The process of claim 10 wherein said reaction is carried out in a non-hydroxylic organic solvent.

12. The process of claim 11 wherein R'' comprises a radical selected from the group consisting of radicals represented by the general formula

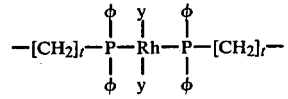

wherein t is an integer of from about 1 to about 10, y is a ligand capable of coordinating with Rh and said hydroformylation catalyst is represented by the general formula $$Zr[O_3P(CH_2)_tP(\phi)_2]_2Rh(y)_2.$$

13. The process of claim 12 wherein y is selected from the group consisting of CO and Cl$^-$, and mixtures thereof.

* * * * *